United States Patent

Cueva

Patent Number: 5,375,594
Date of Patent: Dec. 27, 1994

[54] REMOVABLE MEDICAL ELECTRODE SYSTEM

[76] Inventor: Roberto A. Cueva, 10524 Gretler Pl., La Mesa, Calif. 91941

[21] Appl. No.: 38,521

[22] Filed: Mar. 29, 1993

[51] Int. Cl.⁵ .................................................. A61B 5/04
[52] U.S. Cl. ...................................... 128/642; 607/118
[58] Field of Search ............................... 128/642, 644; 607/116–119, 129, 130, 137, 149

[56] References Cited

U.S. PATENT DOCUMENTS

| | | | |
|---|---|---|---|
| 4,177,818 | 12/1979 | De Pedro | 607/130 |
| 4,920,979 | 5/1990 | Bullara | 607/118 |
| 5,143,067 | 9/1992 | Rise et al. | 607/118 |
| 5,251,634 | 10/1993 | Weinberg | 607/117 |

FOREIGN PATENT DOCUMENTS 0134367  3/1985  European Pat. Off. ............ 607/130

Primary Examiner—Lee S. Cohen
Attorney, Agent, or Firm—David J. Harshman

[57] ABSTRACT

A removable medical electrode system for monitoring electrical activity of selected tissue comprises a flexible member of electrically insulating material shaped to conform to a surface of the tissue. It includes a mechanism for articulating the electrode between an expanded and contracted position to place and remove the electrode on the tissue, and to hold the electrode in place during an operation. An electrical conductor is fixed to the electrode to carry electrical impulse signals from the nerve tissue to a monitoring system.

9 Claims, 2 Drawing Sheets

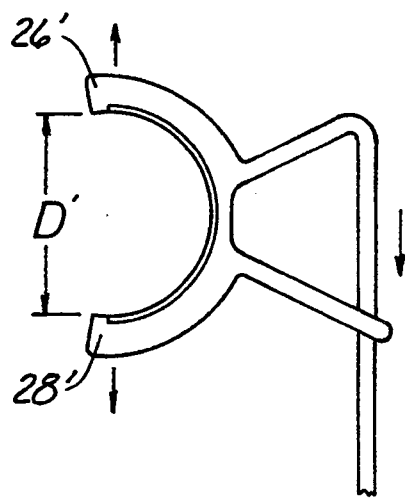
FIG. 4
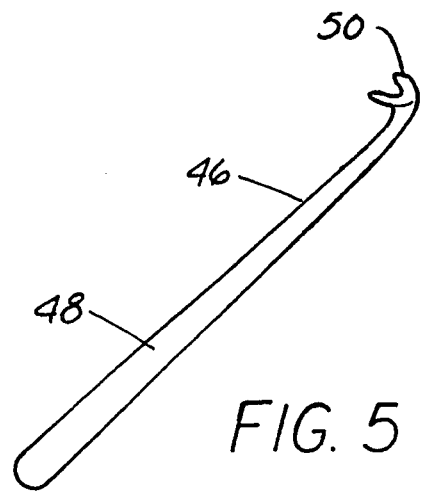
FIG. 5
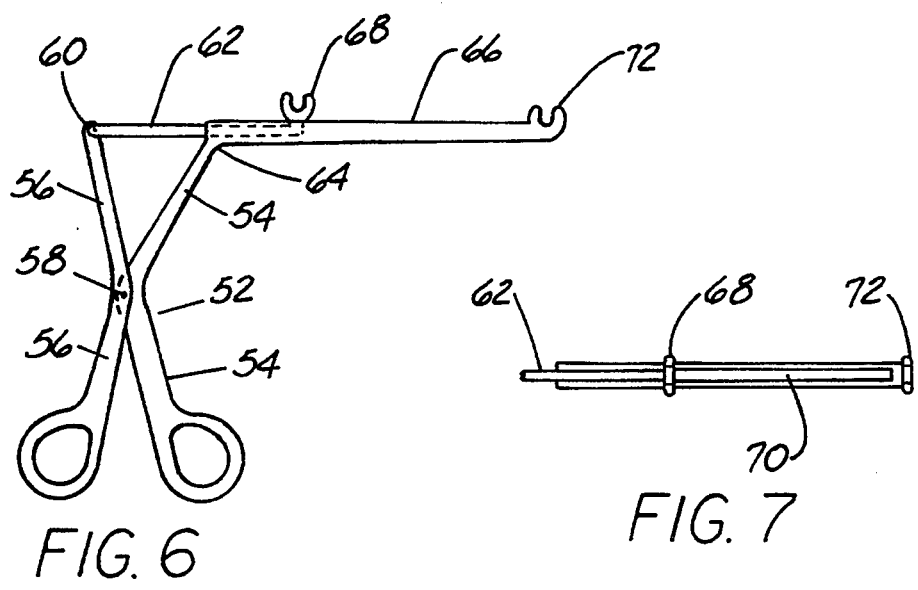
FIG. 6
FIG. 7

REMOVABLE MEDICAL ELECTRODE SYSTEM

BACKGROUND OF THE INVENTION

This invention relates generally to medical devices used to monitor the electrical activity of living tissue. Specifically, this invention relates to an apparatus for atraumatically monitoring the electrical activity of living tissue during a medical procedure to provide information for ensuring that only certain tissue is affected by the procedure, and that surrounding tissue is not. This invention is particularly, though not exclusively, useful in surgical procedures, such as removal of tumors from the eighth cranial nerve without resulting in brain stem injury or interruption of the auditory pathways.

DISCUSSION OF THE PRIOR ART

The use of electrodes to monitor electrical activity of living tissue during surgery is not new. A number of current surgical techniques use systems that monitor the electrical activity of tissue being operated upon so the surgeon can detect any surgical stimulation to selected tissue in order to avoid injury to such tissue. One such surgical procedure is that involving electrophysiologic monitoring of the eighth cranial nerve in the brain stem. In particular, the eighth cranial nerve includes the cochlear nerve which carries auditory impulses from the ear to the brain for hearing, and the vestibular nerve which carries signals from the inner ear to the brain for controlling balance. A conventional technique for monitoring cochlear nerve activity is described in a chapter of a book entitled, *Auditory Function*.

Eighth nerve monitoring to avoid trauma to the cochlear nerve is useful for surgery involving skull-base tumors, intrinsic brain stem lesions, vascular decompression of cranial nerves, vestibular neurectomy, and other procedures concerning the eighth cranial nerve. In such operations it is important to monitor the eighth nerve action potential generated by the intracochlear auditory nerve of the eighth nerve following an auditory stimulus. It is critical that the electrical impulse detected from the cochlear nerve be timely and accurate, since without rapid feedback the surgeon cannot learn which maneuvers cause injury. Injury is to be avoided to the cochlear nerve during such procedures to avoid impairment of the ability of the patient to hear. Therefore it is critical that the signal detected from the cochlear nerve be an accurate representation of the electrical activity in said nerve. Thus by monitoring the wave forms of the feedback signal from the nerve, the surgeon can detect the presence of good wave forms during the procedure.

Unfortunately, in current state-of-the-art procedures for monitoring such wave forms, there are a number of pitfalls. For example, in current procedures the conventional electrode that is used is a cotton-tipped Teflon-insulated silver wire electrode which is placed against the cochlear nerve, and loosely held in place. It must be appreciated that the area within which the surgeon must work is very constricted, and further that the area near the brain stem within the skull is very constricted. During the procedure, the electrical auditory activity is monitored and any changes in amplitude, waveform, or latency, of eighth nerve potentials are noted. If significant, the surgeon ceases any surgical procedures until the waveforms return or become stabilized.

A number of technical problems arise with conventional apparatus for eighth nerve monitoring. Such problems include the fact that the current electrodes routinely become displaced during surgery. This often results from the fact that cerebrospinal fluid pulsates with the heart beat moving the cotton tufted electrode, and possible touching of the electrode by the surgeon. In addition, electrical noise and acoustic drill noise from the surgical operation can cause error in the signals when good solid contact is not maintained with the nerve tissue. Moreover, electrical sensitivity is decreased by spinal fluid pooling between the nerve and the electrode. As noted above, normal brain pulsations and flow of cerebro-spinal fluid or irrigation can dislodge the cotton material electrode from its recording position on the eighth cranial nerve. Such displacement of the electrode may also reduce the signal-to-noise ratio, cause periodic changes in wave form amplitude, and even cause the total loss of the electrical monitoring signal. Therefore, there is a pressing need for a satisfactory electrode.

There are a number of different medical electrodes disclosed in the prior art. However, a disadvantage of such electrodes is that many of them are designed to be implanted into nerve or other tissue, and are therefore not desirable since they are traumatic and cause permanent injury to the nerve. Many such electrodes are made with varying designs to be implanted into the cochlea to stimulate the ganglion of the cranial nerve to achieve hearing. These would not be suitable to monitor cochlear nerve function. Several examples of such electrodes are those disclosed in U.S. Pat. Nos. 3,955,560, 3,999,555, 4,011,875, 4,052,754, 4,177,818, 4,280,513, 4,304,453, 4,565,200, 4,660,571, 4,819,647, 4,850,359, 4,852,573, 4,898,183, 4,903,702, 4,923,469, 5,061,282, 5,131,854, 5,092,332, and 5,095,905.

One such implantable neural electrode is that disclosed in U.S. Pat. No. 5,095,905 to Klepinski which discloses a chronically implantable electrode having a plurality of semi-rigid fingers connected to a spine to envelop the nerve in a hollow cylinder. The inside of the cylinder incorporates a conductor on the inside of the flexible fingers which surround the nerve. The disadvantage of this electrode, however, is that it is permanently implanted and that it completely encircles the nerve. Thus it is not suited for temporary placement and removal. Moreover, its large size and difficulty in placement and removal makes it impractical for use in the type of electrical monitoring during surgical procedures as mentioned above.

In light of the above, the present invention recognizes the need for a medical electrode system which fits snugly on the selected tissue to be electrically monitored, yet can be easily placed upon and removed from the selected tissue. Accordingly, it is an object of the present invention to provide a removable medical electrode system that may readily be placed upon selected tissue to provide an accurate signal representing the electronic activity of the tissue. It is yet another object of the present invention to provide a removable medical electrode system which can be used to monitor electrical activity during surgical and medical procedures, yet may be easily removed without causing any trauma. It is yet another object of the present invention to provide a removable medical electrode system which can be successfully used on selected tissue which may be very sensitive such as that involving the cranial nerves near the brain stem. It is yet another object of the present invention to provide a removable medical electrode system which is durable and reliable, and which is simple and convenient to use. Another object of the present invention is to provide a removable medical electrode system which is easily manufactured and cost effect in use.

SUMMARY OF THE INVENTION

A preferred embodiment of the medical electrode system for monitoring electrical activity of selected tissue comprises a semi-rigid member of insulating material. The semi-rigid or flexible member has an inner surface shaped to conform to a surface of the tissue being monitored, and has a circumferential length sufficient to cover an arc of more than 180 degrees but less than 360 degrees for engaging the tissue. An electrical conductor is affixed to the inner surface of the member. A wire or other electrical coupling is connected to the electrical conductor to connect it to an electrical circuit. Associated with the flexible arcuate member and the electrical coupling mechanism is an actuator means for moving the arcuate member between an expanded position for atraumatically applying and removing said electrode to and from said tissue, and a contracted, position for engaging said electrode on said tissue. In a preferred embodiment,, the actuating means includes a leg mounted to the arcuate member, having a line extending from the distal end of the leg which carries the electrical coupling wire. A guide pin is connected to the arcuate member having a guide hole at a distal end through which the wire passes for slidably carrying the line to establish reciprocal movement of the distal end of the leg with respect to the distal end of the guide post. Pulling on the wire thus reciprocates the arcuate member between the expanded and contracted positions remotely.

In another embodiment, there is included an applicator, such as a wand or pliers for expanding the electrode for positioning the electrode for engagement on the tissue. The actuator facilitates actuation of the electrode between the expanded and contracted positions to allow remote placement and removal of the electrode.

The novel features of this invention, as well as the invention, both as to its structure and its operation will be best understood from the accompanying drawings, taken in conjunction with the accompanying description, in which similar reference characters refer to similar parts.

BRIEF DESCRIPTION OF THE DRAWINGS

FIG. 4 is a side view of the medical electrode system shown in FIG. 3 in an expanded position;

FIG. 5 is a perspective view of one embodiment of a placement device for positioning the medical electrode on selected tissue;

FIG. 6 is an alternative embodiment of a placement device for positioning the medical electrode on selected tissue; and FIG. 7 is a top view of a portion of the apparatus shown in FIG. 6.

DESCRIPTION OF THE PREFERRED EMBODIMENTS

Figure 1:
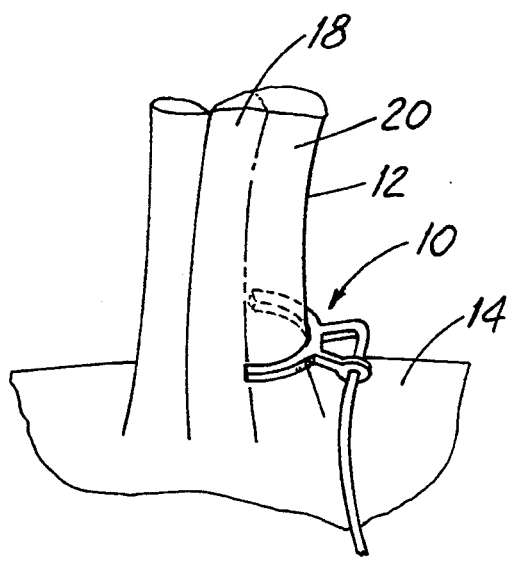
FIG. 1 is a perspective view of a preferred embodiment of a medical electrode shown in its intended operating environment placed on a patient's eighth cranial nerve near the patient's brain stem.

Referring now to FIG. 1 there is shown a removable medical electrode 10 positioned on eighth cranial nerve 12. Eighth cranial nerve 12 extends from brain stem 14 to the inner ear (not shown), which is involved in controlling the sense of hearing and maintaining balance. Eighth cranial nerve 12 is a generally cylindrical nerve that abuts the seventh cranial nerve 16 which controls electrical impulse signals from the brain to facial muscles.

As shown in FIG. 1, eighth cranial nerve 12 is bifurcated into two nerve portions. Vestibular portion 18 of the eighth cranial nerve 12 is for transmitting electrical impulses from the vestibular portion of the inner ear to the brain for controlling the sense of balance. The inferior aspect of the eighth cranial nerve is cochlear division or portion 20 for transmitting electrical impulses from the cochlear portion of the inner ear to the brain stem for maintaining the auditory or hearing function. Monitoring of the electrical activity of the cochlear division or portion of the eighth cranial nerve is important to assist the surgeon in carrying out a number of medical procedures including acoustic neuroma resection, meningioma resection, vestibular neurectomy, posterior fossa aneurysms, vascular decompression of cranial nerves, intrinsic brain stem lesions, clival and skull base tumors, arteriovenous malformations, and epidermoid resections. All of the above procedures are ones in which surgical cutting may take place near the cochlear nerve, yet striving to avoid injury or interruption of the functioning of the cochlear nerve. In addition, it can be appreciated that it is difficult to gain access to this portion of the nerve since it is typically in the skull at the base of the neck, and there is not much room for the surgeon to manipulate and operate. Therefore, precision in cutting is very critical.

For example, one procedure may require, that vestibular nerve portion 18 be cut without any damage to cochlear nerve portion 20. As shown in FIG. 1, medical electrode 12 is positioned near the base of cochlear portion 20 near brain stem 14.

Figure 2:
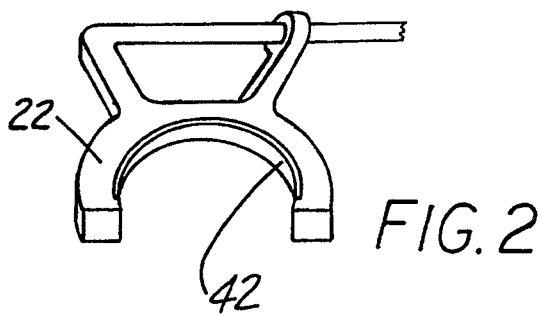
FIG. 2 is a perspective end view of the medical electrode in accordance with the present invention.
Figure 3:
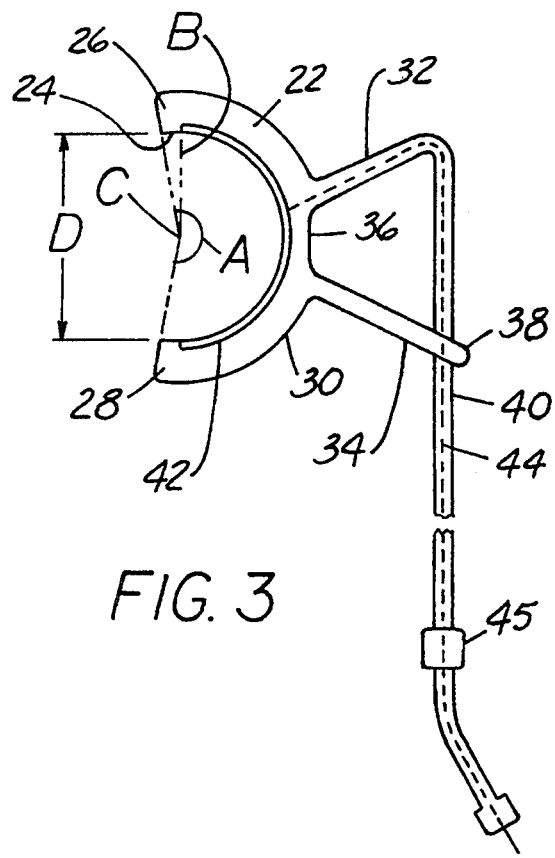
FIG. 3 is a side view of a preferred embodiment of the medical electrode normal contracted position.

Referring now to FIGS. 2 and 3 there is shown in more detail, medical electrode 10. In particular, metrical electrode 10 compresses an elastically flexible member 22 made of electrically insulating material such as a bio-compatible polymer material. Flexible member 22 has an inner surface 24 shaped to conform to the surface of the tissue to be monitored. In the embodiment illustrated, member 22 has a substantially arcuate shape for monitoring the cochlear portion 20 of eighth cranial nerve 12 as shown in FIG. 1. Flexible member 22 includes opposed grasping portions 26 and 28 being diametrically opposed to allow grasping of eighth cranial nerve 12. Flexible member 22 is shown as an arcuate section extending through obtuse angle about center point C. As shown in FIG. 2, member 22 is arcuate and extends through a total arch of slightly greater than 180 degrees to allow grasping portions 26, 28 to grasp eighth cranial nerve 12, but not so much in excess of 180 degrees as to cause grasping portions 26 and 28 to interfere with easy placement and removal of medical electrode 10, as further explained below.

Attached to rear side 30 of medical electrode 10 is a leg 32 extending therefrom, and a guide post 34 for actuating and/or articulating flexible member 22. In the embodiment shown, there is a narrowed, (elastic flex portion 36 located between leg 32 and guide post 34 to facilitate articulation of the flexible member 22. Guide post 34 includes at one end a guide channel 38. Connected to leg 32 is a flexible line 40 which passes through guide channel 38. Flexible member 22 is shown as an arcuate section extending through obtuse angle A about center point C.

Referring further to FIGS. 2 and 3, inner surface 24 of flexible member 22 carries an electrical conductive strip 42. Strip 42 is an electrical conductive material, such as silver, which engages the tissue being monitored to detect the electrical activity of the tissue. Connected to electrically conductive strip 42 is an electrical conductor or wire 44 for transmitting the electrical impulses from strip 42 out to an electrical circuit that monitors the electrical impulses carried from the strip through the wire to generate data used for a conventional system (not shown) to detect the electrical activity. Wire 44 extends from strip 42 through leg 32 and through line 40 out to a conventional monitoring system. Strip 42 extends along inside surface 24 of flexible member 22 through an arc of approximately 180 degrees as shown by angle B in FIG. 2. In the embodiment shown, the conductive strip 42 covers an angle that assures that the electrical activity of essentially all, but only that,, of the tissue to be monitored, which is in this embodiment the cochlear section 20 of eighth cranial nerve 12. This assures a more accurate electrical signal to increase the efficiency of the system. Conductive strip 42 may cover a lesser or greater angle depending on other applications and embodiments.

Referring now to FIGS. 3 and 4, there is shown the representation of the articulation of the arcuate member 22 for placing the electrode 10 onto and removing it from the eighth cranial nerve 12. In particular, in FIG. 3, the electrode 10 is shown in its normal resting or contracted position, having a distance D between portions 26 and 28. In FIG. 4, medical electrode 10 is shown in an expanded position in which the opposed grasping portions 26' and 28' have been expanded to a distance D' to allow medical electrode 10 to be placed onto or removed from cochlear nerve portion 20. By holding guide post 34 in a stationary position and pulling on line 40, leg 32 is urged toward guidepost 34, thereby urging opposed grasping portions 26 and 28 apart to expanded positions 26' and 28'. The increase from the contracted distance D to expanded distance D' allows atraumatic and easy removal and placement of the electrode 10 onto cochlear nerve portion 20.

Further, since conductive wire 44 is incorporated into flexible line 40, and integrated with leg 32, it can readily be seen that medical electrode 10 can be actuated mechanically from a remote position. This is important in the process of surgical procedures in which there is not much room, and especially with respect to the eighth cranial nerve in which it is necessary to approach the nerve typically at a right angle in order to facilitate the placement of the electrode.

In FIG. 5 there is shown one embodiment of an electrode placement wand 46. Wand 46 comprises a long, narrow handle 48 and a yoke 50 at one end thereof. Yoke 50 is adapted to engage and abut guide channel 38 so as to permit line 40 to be pulled through guide channel 38 and yoke 50 to urge leg 32 toward and away from guide post 34. This actuates electrode 10 between its expanded and contracted positions. Thus, the wand 46 can be used to facilitate holding, placement, and removal of electrode 10.

Another embodiment of an applicator for positioning and actuating the electrode is shown in FIG. 6. An electrode placement apparatus 52 comprises a pair of articulating members 54 and 56 which are pivotally connected at juncture 58. At end 60 of member 56 there is pivotally connected a long, slender rod 62. At the end of rod 62, there is a catch 68 which protrudes from rod 62. At distal end 64 of member 54, there is rigidly connected a tapered cylinder 66 for slidably carrying rod 62. Cylinder 66 includes a longitudinal slot 70 on its upper surface seen in perspective view FIG. 7. The distal end of cylinder 66 has a yoke 72 adapted to abut guide channel 38.

In operation, articulation of members 54 and 56 of placement apparatus 52 causes catch 68 to reciprocate toward and away from yoke 72. When yoke 72 is positioned against guide channel 38 and catch 68 is engaged with bead 45 on wire 40, articulation of placement apparatus 52 causes wire 40 to move back and forth through guide post 38 to articulate the electrode 10. Due to the structure of the present system, the electrode 10 can be easily manipulated and moved to its expanded position for placement and removal of the electrode on selected nerve and other tissue. When medical electrode 10 is in place and released to its contracted position, it holds snugly yet atraumatically by elastic memory and appropriate sizing of the electrode 10 to match the diameter of the tissue to be monitored.

Figure 8:
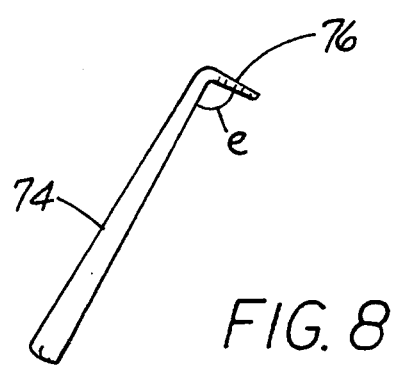
FIG. 8 is an embodiment of a device for estimating the diameter the tissue being monitored in accordance with the present invention.

In FIG. 8, there is shown a tissue diameter estimating tool 74 having a measuring portion 76 forming approximately a 90 degree angle at angle E. Measuring portion 76 has increments of measure indicated thereon, such as millimeters for estimating the diameter of the particular tissue to be monitored, such as neural or muscular tissue. By manufacturing a set of medical electrodes 10 in a series of standardized sizes, then a set of medical electrodes can be selected from to achieve the best fit for the particular tissue to be monitored. In accordance with the present invention, due to the super or design and structure thereof, there is easy and atraumatic placement and removal of the electrode, yet there is excellent electrode stability on the nerve during the operation. Moreover, the device is ambidextrous so there is no need for specific right or left designs with the present invention.

While the particular medical electrode system as hereon shown and disclosed in detail is fully capable of obtaining the objects and providing the advantages hereinbefore stated, it is to be understood that it is merely illustrative of the presently-preferred embodiments of the invention, and that no limitations are intended to the details of construction or design herein shown other than as defined in the appended claims.

I claim:

1. An atraumatic removable medical electrode system for monitoring electrical activity of selected tissue, comprising:
   a flexible member of electrically insulating material having an inner surface shaped to conform to a surface of said tissue, said member having a circumferential length sufficient to cover an arc of more than 180 degrees, but less than 360 degrees, for engaging said tissue;

an electrical conductor affixed to said inner surface of said member;

means for electrically coupling said conductor to an electrical circuit; and actuating means connected to said member for moving said member between a contracted position for holding said electrode on said tissue, and an expanded position for placing said electrode onto and removing said electrode from said tissue.

2. The electrode system of claim 1, wherein said electrical conductor covers an arc substantially equal to an arc sufficient to cover the surface of the tissue being monitored.

3. The electrode system of claim 1, wherein said electrical coupling means is integral with said actuating means.

4. The electrode system of claim 1, wherein said actuating means includes a leg mounted to said member having a line extending from a distal end of said leg, and a guide slidably carrying said line to establish reciprocal movement of said leg to remotely move said member between said expanded and contracted positions.

5. The electrode system of claim 4, wherein said electrical coupling means is carried in said leg and said line.

6. The electrode system of claim 5, wherein said member includes an elastic flex portion.

7. The electrode system of claim 6, further comprising an applicator having a stationary shaft member and an reciprocating rod member carried on said stationary shaft member, said stationary shaft member having a position for engaging said guide; and said reciprocating rod member having means for holding said line to reciprocate said line.

8. The electrode system of claim 6, further comprising a wand having means for engaging said guide to hold said guide stationary in relation to said line.

9. A removable medical electrode for monitoring electrical activity of a selected portion of tissue comprising:

means for engaging said selected portion of said tissue, said engaging means including a pair of opposed resilient semi-rigid arcuate grasping members shaped for atraumatically holding said engaging means on said tissue portion;

means connected to said engaging means for remotely reciprocating said resilient semi-rigid arcuate grasping members between a contracted position wherein said members are spaced apart a first distance to atraumatically grasp said tissue portion, and an expanded position wherein said grasping members are spaced apart a second distance to permit atraumatic application and removal of said electrode to and from said tissue portion; and means for electrically connecting said engaging means to an electrical circuit.

* * * * *